United States Patent
Shin et al.

(10) Patent No.: US 11,673,992 B2
(45) Date of Patent: Jun. 13, 2023

(54) ISOCYANATE COMPOSITION WITH IMPROVED STABILITY AND REACTIVITY, AND OPTICAL LENS USING SAME

(71) Applicant: SKC CO., LTD., Gyeonggi-do (KR)

(72) Inventors: Junghwan Shin, Gyeonggi-do (KR); Jung Hwan Myung, Gyeonggi-do (KR); Hyuk Hee Han, Gyeonggi-do (KR)

(73) Assignee: SKC CO., LTD., Gyeonggi-do (KR)

( * ) Notice: Subject to any disclaimer, the term of this patent is extended or adjusted under 35 U.S.C. 154(b) by 383 days.

(21) Appl. No.: 16/954,076

(22) PCT Filed: Dec. 26, 2018

(86) PCT No.: PCT/KR2018/016621
§ 371 (c)(1),
(2) Date: Jun. 15, 2020

(87) PCT Pub. No.: WO2019/132491
PCT Pub. Date: Jul. 4, 2019

(65) Prior Publication Data
US 2021/0163669 A1      Jun. 3, 2021

(30) Foreign Application Priority Data

Dec. 27, 2017 (KR) .......................... 10-2017-0180889

(51) Int. Cl.
| | | |
|---|---|---|
| C08G 18/75 | (2006.01) | |
| C07C 265/02 | (2006.01) | |
| C08G 18/64 | (2006.01) | |
| C08K 5/03 | (2006.01) | |
| G02B 1/04 | (2006.01) | |
| C07C 265/08 | (2006.01) | |
| C07C 265/12 | (2006.01) | |

(52) U.S. Cl.
CPC .......... *C08G 18/757* (2013.01); *C07C 265/02* (2013.01); *C07C 265/08* (2013.01); *C07C 265/12* (2013.01); *C08G 18/6453* (2013.01); *C08K 5/03* (2013.01); *G02B 1/041* (2013.01)

(58) Field of Classification Search
CPC .... C07C 265/02; C07C 265/08; C07C 265/12
See application file for complete search history.

(56) References Cited

U.S. PATENT DOCUMENTS

| | | | |
|---|---|---|---|
| 3,660,456 A * | 5/1972 | Naito .................... | C07C 265/14 560/331 |
| 5,302,749 A | 4/1994 | Nagata et al. | |
| 5,576,412 A * | 11/1996 | Hirata .................... | C08G 18/70 528/65 |
| 5,728,317 A | 3/1998 | Laqua et al. | |
| 2015/0274760 A1 * | 10/2015 | Spyrou ................. | C08G 18/34 556/401 |

FOREIGN PATENT DOCUMENTS

| | | |
|---|---|---|
| CN | 104718215 A | 6/2015 |
| GB | 1254690 A | 11/1971 |
| JP | H5-078304 A | 3/1993 |
| JP | 07-033851 A | 2/1995 |
| JP | 2001-354640 A | 12/2001 |
| JP | 2004-285359 A | 10/2004 |
| JP | 2014-055229 A | 3/2014 |
| JP | 2014-234429 A | 12/2014 |
| KR | 10-2009-0082371 A | 7/2009 |
| KR | 2012-0076329 | 7/2012 |
| KR | 10-2015-0063573 A | 6/2015 |
| KR | 10-1842254 B1 | 3/2018 |

OTHER PUBLICATIONS

Office Action issued by the Japanese Patent Office dated Feb. 22, 2022.
Office Action issued by the Chinese Patent Office dated Sep. 1, 2021.
Office Action issued by the Japanese Patent Office dated Jun. 8, 2021.

* cited by examiner

*Primary Examiner* — Michael L Leonard
(74) *Attorney, Agent, or Firm* — IP & T Group LLP

(57) ABSTRACT

An embodiment relates to an isocyanate composition with improved stability and reactivity and a plastic optical lens using the same. The isocyanate composition has improved stability since the content of chlorine in the composition is adjusted to 22-500 ppm, and thus the isocyanate composition can prevent the deterioration in reactivity even in the long-term storage. Therefore, the isocyanate composition according to an example, even when used after long-term storage after preparation, can be prepared, through polymerization with a thiol-based compound, as a polythiourethane-based optical material with excellent physical properties, such as refractive index, Abbe number, transparency, glass transition temperature, and yellowness, and thus the isocyanate composition is useful in fields of glass lenses, a camera lens, and the like.

13 Claims, No Drawings

ISOCYANATE COMPOSITION WITH IMPROVED STABILITY AND REACTIVITY, AND OPTICAL LENS USING SAME

This application is a national stage application of PCUKR2018/016621 filed on Dec. 26, 2018, which claims priority of Korean patent application numbers 10-2017-0180889 filed on Dec. 27, 2017. The disclosure of each of the foregoing applications is incorporated herein by reference in its entirety.

TECHNICAL FIELD

Embodiments relate to an isocyanate composition with improved stability and reactivity and an optical lens prepared therefrom.

BACKGROUND ART

Since plastics optical materials are lightweight, hardly breakable, and excellent in dyeability as compared with optical materials made of inorganic materials such as glass, they are widely used as optical materials for eyeglass lenses, camera lenses, and the like. Recently, there has been a demand for optical materials having higher performance in terms of high transparency, high refractive index, low specific gravity, high heat resistance, and high impact resistance.

Polythiourethanes among plastic optical materials are widely used as an optical material by virtue of their excellent optical characteristics and excellent mechanical properties. A polythiourethane may be prepared by reacting a thiol and an isocyanate. The physical properties of the thiol and/or the isocyanate may significantly affect the physical properties of the polythiourethane to be prepared. In general, lenses produced from polythiourethanes are widely used since they have a high refractive index, a lightweight, and a relatively high impact resistance. But they have disadvantages in that bubbles are generated in the polymerization reaction of a thiol and an isocyanate, the reactivity is reduced, a side reaction takes place, or it is not easy to control the polymerization rate.

Studies have continued to enhance the optical properties of lenses by varying the types and contents of thiols and/or isocyanates as raw materials of a polythiourethane. For example, there has been an attempt to enhance the transparency of a lens by controlling the polymerization rate during polymerization by adjusting the content of water in a thiol (Korean Patent Laid-open Publication No. 2012-0076329).

In addition, a method of controlling the polymerization reaction by adjusting the kind and physical properties of an isocyanate is widely known. Isocyanates used in the polymerization of a polythiourethane are generally prepared by reacting an aliphatic or aromatic amine with phosgene. For example, xylenediamine, cyclohexyl dimethylamine, or the like may be reacted with phosgene to obtain xylene diisocyanate, hydrogenated xylylene diisocyanate ($H_6XDI$), or the like (i.e., phosgene process). Alternatively, it may be reacted with a compound having an alkylcarbonate or alkylhalocarbonyl group other than phosgene (i.e., non-phosgene process).

An isocyanate obtained by the phosgene process is usually purified by distillation. This is intended not only to remove impurities in the isocyanate produced immediately after the reaction but also to prevent the side reaction to produce the dimer or trimer by the self-reaction of the NCO groups in the isocyanate.

For example, although xylylene diisocyanate is widely used since it has a rapid curing rate and a low level of yellowing at the time of preparing lenses, it has disadvantages in that it is difficult for a product produced therefrom to have uniform characteristics because of the high reactivity of the NCO groups and that it is liable to lose its original physical properties due to side reactions when it is stored for a long period of time. In addition, not only is a side reaction by the self-reaction of the NCO groups involved, but also the content of the NCO groups may be changed, which may affect the reactivity. As a result, there may be a problem that a solid material is precipitated, or this phenomenon is further accelerated by the reaction with moisture introduced from the environment. Various stabilizers may be used to prevent or retard such problems, but this may cause yellowing or other problems in the production of polythiourethane as they affect the reactivity. In addition, unlike other types of isocyanates, xylylene diisocyanate has a much greater side effect depending on the kinds and contents of additives, which makes it difficult to find an optimal formulation. There is a growing demand for highly stable isocyanates to overcome these disadvantages.

DISCLOSURE OF THE INVENTION

Technical Problem

When xylylene diisocyanate is used in the production of an optical material, various kinds of side reactions may take place due to its high reactivity, which may generate a solid material and have a serious impact on the optical characteristics of the optical material. In order to resolve this problem, attempts have been made to reduce the impurities in xylylene diisocyanate, which may affect the reactivity, to a very minute amount. However, it is commercially very difficult to reduce the amount of impurities to the maximum, and it also incurs a large amount of expenses to operate such a process. As a result of researches, the inventors of the present invention have found that if a hydrogenated xylylene diisocyanate ($H_6XDI$) composition contains a certain amount of chlorine, it may improve the stability and prevents the degradation of the reactivity.

Accordingly, an embodiment aims to provide a xylylene diisocyanate composition having improved stability and reactivity by adjusting the amount of chlorine to a specific range, and a process for preparing the same.

In addition, an embodiment aims to provide a polymerizable composition using the xylylene diisocyanate composition, an optical material, and a process for producing a plastic optical lens.

Solution to the Problem

According to an embodiment, there is provided an isocyanate composition, which. comprises a chlorine-based storage stabilizer and hydrogenated xylylene diisocyanate ($H_6XDI$), wherein the content of chlorine derived from the chlorine-based storage stabilizer in the entire composition is 22 to 500 ppm, and the content of the NCO groups contained in the entire composition is 42 to 45% by weight.

According to another embodiment, there is provided an isocyanate composition, which comprises a chlorine-based storage stabilizer and hydrogenated xylylene diisocyanate ($H_6XDI$), Wherein the content of the NCO groups contained in the entire composition is 42 to 45% by weight, and when the composition is sealed and left in a container, the region of which in contact with the composition is not reactive with chlorine, at a temperature of 80° C. for 6 months, the difference in the content of the NCO groups between the initial composition and the composition after 6 months is 4% by weight or less.

According to still another embodiment, there is provided a process for preparing an isocyanate composition, which comprises (I) producing a composition that comprises hydrogenated xylylene diisocyanate ($H_6XDI$) from cyclohexyidi(methylamine) by a process for synthesizing an isocyanate; and (2) adjusting the content of chlorine contained in the composition that comprises hydrogenated xylylene diisocyanate to 22 to 500 ppm, wherein when the composition that comprises $H_6XDI$ is sealed and left in a container, the region of which in contact with the composition is not reactive with chlorine, at a temperature of 80° C. for 6 months, the difference in the content of the NCO groups between the initial composition and the composition after 6 months is 4% by weight or less.

According to still another embodiment, there is provided a polymerizable composition, which comprises an isocyanate composition and a thiol-based compound, wherein the isocyanate composition comprises a chlorine-based storage stabilizer and hydrogenated xylylene diisocyanate ($H_6XDI$), the content of chlorine derived from the chlorine-based storage stabilizer in the isocyanate composition is 22 to 500 ppm, and the content of the NCO groups contained in the isocyanate composition is 42 to 45% by weight.

According to still another embodiment, there is provided an optical lens, which. comprises a polythiourethane formed by curing a polymerizable composition that comprises an isocyanate composition and a thiol-based compound, wherein the isocyanate composition comprises a chlorine-based storage stabilizer and hydrogenated xylylene diisocyanate ($H_6XDI$), the content of chlorine derived from the chlorine-based storage stabilizer in the isocyanate composition is 22 to 500 ppm, and the content of the NCO groups contained in the isocyanate composition is 42 to 45% by weight.

According to still another embodiment, there is provided a process for producing an optical lens, which comprises (A) providing an isocyanate composition, (B) providing a thiol-based compound, (C) providing a polymerizable composition that comprises the isocyanate composition and the thiol-based compound, and (D) curing the polymerizable composition, wherein the isocyanate composition comprises a chlorine-based storage stabilizer and hydrogenated xylylene diisocyanate ($H_6XDI$), the content of chlorine derived from the chlorine-based storage stabilizer in the isocyanate composition is 22 to 500 ppm, and the content of the NCO groups contained in the isocyanate composition is 42 to 45% by weight.

Advantageous Effects of the Invention

The isocyanate composition according to the embodiments contains a certain amount of chlorine to improve the stability, so that the degradation of the reactivity can be prevented even when it is stored for a long period of time.

Therefore, even if the isocyanate composition according to the embodiments is used after storage thereof for a long period of time after the preparation thereof, the isocyanate composition can be polymerized with a thiol to produce a polythiourethane-based optical material that has excellent properties in terms of refractive index, Abbe number, transparency, glass transition temperature, yellow index, and the like. It can be advantageously used for eyeglass lenses, camera lenses, and the like.

Best Mode for Carrying out the Invention

Hereinafter, the present invention will be described in detail with reference to the embodiments. The embodiments are not limited to those described below. Rather, they may be modified into various forms as long as the gist of the invention is not altered.

In this specification, when a part is referred to as "comprising" an element, it is to be understood that the part may comprise other elements as well.

In addition, all numbers and expression related to the quantities of components, reaction conditions, and the like used herein are to be understood as being modified by the term "about," unless otherwise indicated.

An embodiment provides an isocyanate composition, which comprises a chlorine-based storage stabilizer and hydrogenated xylylene diisocyanate ($H_6XDI$), wherein the content of chlorine derived from the chlorine-based storage stabilizer in the entire composition is 22 to 500 ppm, and the content of the NCO groups contained in the entire composition is 42 to 45% by weight.

Specifically, the chlorine-based storage stabilizer can further stabilize the reactivity of $H_6XDI$, to thereby enhance the storage stability of $H_6XDI$.

The chlorine-based storage stabilizer may be a chlorine ion or a compound represented by the following Formula 1 or 2:

[Formula 1]
R1—R2—(Cl)$_n$

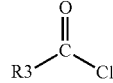

[Formula 2]

In the above formulae, n is an integer from 1 to 3, R1 is $C_{6-10}$ aryl optionally substituted with halogen, hydroxy, or amino, R2 is $C_{1-10}$ alkylene, R3 is $C_{6-10}$ aryl optionally substituted with halogen, hydroxy, or amino, or $C_{1-10}$ alkyl optionally substituted with halogen, hydroxy or amino.

Specifically, the chlorine-based storage stabilizer may comprise at least one chlorine-based storage stabilizer selected from the group consisting of benzotrichloride (Formula 3), benzyl chloride (Formula 4), benzoyl chloride (Formula 5), and a $C_{1-10}$ alkanoyl chloride (Formula 6):

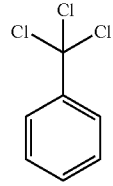

[Formula 3]

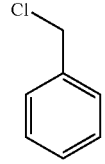

[Formula 4]

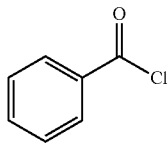

[Formula 5]

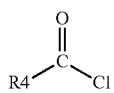

[Formula 6]

In the above Formula 6, R4 is $C_{1-10}$ alkyl.

It is important to control the content of chlorine contained in the isocyanate composition to an appropriate level.

Specifically, the content of chlorine contained in the isocyanate composition, that is, the content of chlorine derived from the chlorine-based storage stabilizer may be about 22 to 600 ppm, about 22 to 500 ppm, about 24 to 500 ppm, about 30 to 500 ppm, or about 50 to 500 ppm. If the content of chlorine in the isocyanate composition is within the above range, it is excellent in long-term storage stability and optical characteristics. More specifically, if the content of chlorine in the isocyanate composition is less than the above range, the high reactivity of $H_6XDI$ cannot be effectively suppressed, so that cloudiness and precipitates may occur due to such side reactions as the self-reaction between the NCO groups when the composition is stored for a long period of time. If it exceeds the above range, it may cause yellowing due to an excessive amount of chlorine or a chlorine-based compound.

The chlorine content refers to the total amount of the chlorine components contained in the isocyanate composition, that is, the chlorine ions derived from the chlorine-based storage stabilizer and the chlorine components contained in the chlorine-based compounds, which may be measured by a method such as combustion ion chromatography.

The content of the NCO groups contained in the isocyanate composition may be 42 to 45% by weight or 43 to 45% by weight. The above NCO content range is close to the theoretical NCO content in which the self-reaction between the NCO groups in an isocyanate composition would not take place. Within the above range, the physical properties of the isocyanate composition according to the embodiment may not be deteriorated.

The NCO content (NCO %) refers to a value converted from the weight in percent of the free NCO (reactive NCO) groups contained in the composition, which may be measured by a method such as back titration with hydrochloric acid.

The isocyanate composition whose chlorine content is adjusted as described above is very excellent in storage stability.

For example, when the isocyanate composition is left at a temperature of 80° C. for 6 months, the amount of precipitates generated may be 1% by weight or less, 0.5% by weight or less, or 0.3% by weight or less, based on the total weight of the composition.

In addition, the difference in the content of the NCO groups between the initial composition and the composition left at a temperature of 80° C. for 6 months may be 5% by weight or less, preferably 4% by weight or less, 3% by weight or less, 2% by weight or less, or 1% by weight or less.

Further, the isocyanate composition may be stored in a storage container that is not reactive with chlorine to further enhance the long-term storage stability of the composition. Specifically, when the isocyanate composition is sealed and left in a container, the region of which in contact with the composition is not reactive with chlorine, at a temperature of 80° C. for 6 months, the difference in the content of the NCO groups between the initial composition and the composition after 6 months is 4% by weight or less, preferably 3% by weight or less, 2% by weight or less, or 1% by weight or less.

In such event, the storage container may be coated with at least one of a polymeric coating agent such as epoxy-based, polyethylene-based, fluorine-based (such as Teflon), silicone-based, phenol-based, alkyd-based, polyester-based, acrylic-based, amino-based, vinyl-based coating agents, and the like; or an inorganic metal coating agent such as molybdenum-based, phosphate-based, zinc-based coating agents, and the like.

Accordingly, an embodiment provides an isocyanate composition, which comprises a chlorine-based storage stabilizer and $H_6XDI$, wherein the content of the NCO groups contained in the entire composition is 42 to 45% by weight, and when the composition is sealed and left in a container, the region of which in contact with the composition is not reactive with chlorine, at a temperature of 80° C. for 6 months, the difference in the content of the NCO groups between the initial composition and the composition after 6 months is 4% by weight or less.

The amount of $H_6XDI$ in the isocyanate composition may be 90% by weight or more, 95% by weight or more, or 99% by weight or more, 90% by weight to less than 100% by weight, 95% by weight to less than 100% by weight, or 99% by weight to less than 100% by weight.

Further, an embodiment provides a process for preparing an isocyanate composition, which comprises (1) producing a composition that comprises hydrogenated xylylene diisocyanate ($H_6XDI$) from cyclohexyldi(methylamine) by a process for synthesizing an isocyanate; and (2) adjusting the content of chlorine contained in the composition that comprises hydrogenated xylylene diisocyanate to 22 to 500 ppm, wherein when the composition that comprises $H_6XDI$ is sealed and left in a container, the region of which in contact with the composition is not reactive with chlorine, at a temperature of 80° C. for 6 months, the difference in the content of the NCO groups between the initial composition and the composition after 6 months is 4% by weight or less.

Specifically, according to the above preparation process, a composition that comprises $H_6XDI$ may be obtained from cyclohexyldi(methylamine), specifically (3-(aminomethyl)cyclohexyl)methanamine by an isocyanate synthesis process (a phosgene process or a non-phosgene process) in step (1).

For example, specifically, a composition that comprises $H_6XDI$ may be obtained by reacting (3-(aminomethyl)cyclohexyl)methanamine with phosgene, a halo $C_{1-10}$ alkyl chloroformate, or a halo di-$C_{1-10}$ alkyl carbonate.

According to an example of the phosgene process, as shown in Reaction Scheme 1 below, (3-(aminomethyl)cyclohexyl)methanamine may be reacted with hydrochloric acid at a temperature of 30° C. or lower in an ester-based solvent to obtain an amine hydrochloride, which may then be reacted with phosgene at a temperature of 120 to 170° C., to thereby synthesize $H_6XDI$.

[Reaction Scheme 1]

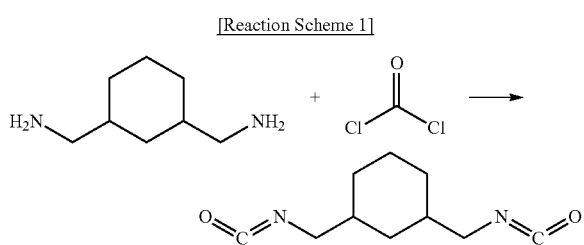

According to an example of the non-phosgene process, as shown in Reaction Scheme 2 below, (3-(aminomethyl)cyclohexyl)methanamine may be reacted with a halo $C_{1-10}$ alkyl chloroformate or a halo di-$C_{1-10}$ alkyl carbonate to prepare a biscarbamate, which may then be thermally decomposed in the presence of a catalyst at a high temperature of 130 to 250° C. in a solvent, to thereby synthesize $H_6XDI$.

[Reaction Scheme 2]

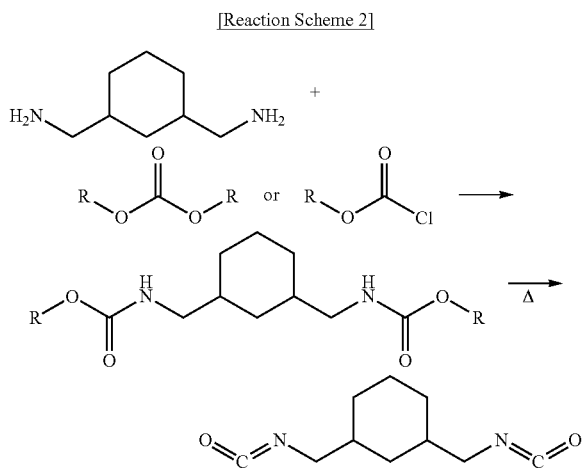

In the above Reaction Scheme 2, R is a halo $C_{1-10}$ alkyl. Here, the halo may be F, Cl, Br, or I.

A composition that comprises $H_6XDI$ is prepared by the above method. In such event, chlorine ions capable of hydrogenation are also produced in the phosgene process, while chlorine ions capable of hydrogenation are not produced in the non-phosgene process. Thus, it is necessary to deliberately adjust the chlorine content in the composition.

In the above step (2), a chlorine-based storage stabilizer is added to the composition comprising $H_6XDI$ and obtained in the preceding step, so that the content of chlorine contained in the composition is adjusted to 22 to 500 ppm, thereby enhancing the storage stability of the composition.

For example, in the above step (2), the adjustment of the chlorine content may be carried out by adding to the composition obtained in the above step (1) at least one chlorine-based storage stabilizer selected from the group consisting of benzotrichloride, benzyl chloride, benzoyl chloride, and a $C_{1-10}$ alkanoyl chloride, or containing chlorine ions. The step of adding a chlorine-based storage stabilizer may be carried out by adding the chlorine-based storage stabilizer to the composition and stirring and mixing the mixture at 20 to 50° C. In such event, the chlorine-based storage stabilizer can be suitably used in a required amount of the compounds exemplified above, Alternatively, in the above step (2), the chlorine content may be adjusted by adding chlorine as a chlorine-based storage stabilizer to the composition obtained in the above step (1), If chlorine is used, this step may be carried out by injecting and dissolving chlorine gas while the composition is stirred at room temperature, and then removing the undissolved chlorine gas under a reduced pressure.

In the above step (2), if the chlorine-based storage stabilizer is excessively present in, or added to, the composition, a step of removing it may be further performed. That is, after the above step (2), a further step is carried out in which the composition is subjected to heat distillation to remove the excess chlorine ion or chlorine-based compound present in the composition, to thereby adjust the chlorine content in the composition to 22 to 500 ppm. In addition, after each of the chlorine addition/removal steps, the chlorine content in the composition may be measured to adjust the chlorine content to 22 to 500 ppm. In such event, if necessary, these steps may be further carried out.

As described above, the isocyanate composition may be contained and stored in a container that is not reactive with chlorine.

Specifically, an embodiment provides an isocyanate composition storage article, which comprises an isocyanate composition and a container that contains the isocyanate composition, wherein the isocyanate composition comprises a chlorine-based storage stabilizer and $H_6XDI$, and the content of the NCO groups contained in the entire composition is 42 to 45% by weight. In such event, the region of the container in contact with the isocyanate composition is not reactive with chlorine.

In the case where the chlorine component in the isocyanate composition is in contact with a reactive substance such as a metal, the concentration of impurities such as metal ions in the isocyanate composition increases over time, and there is a risk of deterioration of the composition. Further, it may have a serious impact on the reactivity of the composition and on the optical characteristics of lenses produced therefrom. Therefore, the storage article according to the embodiment, which uses a container having a contact region that is not reactive with chlorine, can prevent elution of metal ions and the like due to the corrosion of the container.

For example, the region of the container in contact with the isocyanate composition may be made of a non-metal. Specifically, the region of the container in contact with the composition may be coated with at least one of a polymeric coating agent such as epoxy-based, polyethylene-based, fluorine-based (such as Teflon), silicone-based, phenol-based, alkyd-based, polyester-based, acrylic-based, amino-based, vinyl-based coating agents, and the like; or an inorganic metal coating agent such as molybdenum-based, phosphate-based, zinc-based coating agents, and the like.

Since the storage article as described above does not cause a reaction between the container and the composition, materials are hardly eluted from the container into the composition even if the composition is stored therein for a long period of time.

As an example, when the isocyanate composition is sealed and left in the container at a temperature of 80° C. for 6 months, the difference in the content of the NCO groups between the initial composition and the composition after 6 months is 4% by weight or less, and the total amount of the materials eluted from the container may be 0.8 ppm or less, 0.6 ppm or less, or 0.4 ppm or less (see Test Examples 1 and 2).

As another example, when the isocyanate composition is sealed and left in the container at a temperature of 80° C. for 1 month, the difference in the content of the NCO groups between the initial composition and the composition after 1 month is 4% by weight or less, and the total amount of the materials eluted from the container may be 0.8 ppm or less, 0.6 ppm or less, or 0.4 ppm or less.

In addition, an embodiment provides a polymerizable composition, which comprises an isocyanate composition and a thiol-based compound, wherein the isocyanate composition comprises a chlorine-based storage stabilizer and $H_6XDI$, the content of chlorine derived from the chlorine-based storage stabilizer in the isocyanate composition is 22 to 500 ppm, and the content of the NCO groups contained in the isocyanate composition is 42 to 45% by weight.

The polymerizable composition may comprise the isocyanate composition and the thiol-based compound in a mixed state or in a separated state. That is, the isocyanate composition and the thiol-based compound in the polymerizable composition may be in a state of being compounded in contact with each other or separated from each other so as not to contact each other.

The molar ratio of the SH groups to the NCO groups in the polymerizable composition may be 0.5 to 3.0 or 0.8 to 1.3.

The thiol-based compound may be a thiol oligomer or a polythiol and may be used alone or as a mixture of two or more thereof.

Examples of the thiol-based compound may include 3,3'-thiobis[2-[(2-mercaptoethyl)thio]-1-propanethiol], bis(2-(2-mercaptoethylthio)-3-mercaptopropyl) sulfide, 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, bis(2-mercaptoethyl) sulfide, tetrakis(mercaptomethyl)methane, 2-(2-mercaptoethylthio)propane-1,3-dithiol, 2-(2,3-bis(2-mercaptoethylthio)propylthio)ethanethiol, bis(2,3-dimercaptopropal) sulfide, bis(2,3-dimercaptopropanyl) disulfide, 1,2-bis[(2-mercaptoethyl)thio]-3-mercaptopropane, 1,2-bis(2-(2-mercaptoethylthio)-3-mercaptopropylthio)ethane, 2-(2-mercaptoethylthio)-3-2-mercapto-3-[3-mercapto-2-(2-mercaptoethylthio)-propylthio]propylthio-propane-1-thiol, 2,2-bis-(3-mercapto-propionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R,11S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio)propylthio)propylthio)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), trimethylolpropane tris(3-mercaptopropionate), pentaerythritol tetrakis(2-mercaptoacetate), bispentaerythritol-ether-hexakis(3-mercaptopropionate), 1,1,3,3-tetrakis(mercaptomethylthio)propane, 1,1,2,2-tetrakis(mercaptomethylthio)ethane, 4,6-bis(mercaptomethylthio)-1,3-dithiane, pentaerythritol tetrakis(2-mercaptoacetate), pentaerythritol tetrakis(3-mercaptopropionate), and 2-(2,2-bis(mercaptodimethylthio)ethyl)-1,3-dithiane.

In addition, the polymerizable composition may further comprise such additives as an internal mold release agent, an ultraviolet absorber, a polymerization initiator, a heat stabilizer, a correcting agent, a chain extender, a crosslinking agent, a light stabilizer, an antioxidant, and a filler, depending on the purpose thereof.

Examples of the internal mold release agent include a fluorine-based nonionic surfactant having a perfluoroalkyl group, a hydroxyalkyl group, or a phosphate ester group; a silicone-based nonionic surfactant having a dimethylpolysiloxane group, a hydroxyalkyl group, or a phosphate ester group; an alkyl quaternary ammonium salt such as trimethylcetylammonium salt, trimethylstearylammonium salt, dimethylethylcetylammonium salt, triethyldodecylammonium salt, trioctylmethylammonium salt, and diethylcyclohexadodecylammonium salt; and an acidic phosphate ester. It may be used alone or in combination of two or more.

As the ultraviolet absorber, benzophenone-based, benzotriazole-based, salicylate-based, cyanoacrylate-based, oxanilide-based, or the like may be used.

As the polymerization initiator, an amine type, a phosphorus type, an organotin type, an organic copper type, an organic gallium type, an organic zirconium type, an organic iron type, an organic zinc, an organic aluminum, or the like may be used.

As the heat stabilizer, a metal fatty acid salt, a phosphorus compound, a lead compound, or an organotin compound may be used alone or in combination of two or more.

An embodiment provides an optical lens, which comprises a polythiourethane formed by curing a polymerizable composition that comprises an isocyanate composition and a thiol-based compound, wherein the isocyanate composition comprises a chlorine-based storage stabilizer and $H_6XDI$, the content of chlorine derived from the chlorine-based storage stabilizer in the isocyanate composition is 22 to 500 ppm, and the content of the NCO groups contained in the isocyanate composition is 42 to 45% by weight.

The polythiourethane as a raw material of the optical lens may be prepared by polymerizing (and curing) the isocyanate composition whose chlorine content is adjusted as described above and the thiol-based compound. In such event, the molar ratio of the SH groups to the NCO groups in the polymerization reaction may be 0.5 to 3.0 or 0.8 to 1.3.

In addition, a reaction catalyst, which is conventionally used in the production of polythiourethane, may be employed in order to control the reaction rate in the polymerization reaction. The catalyst can simultaneously perform the role of a polymerization initiator and a curing catalyst. As the catalyst, a tin-based catalyst may be used. For example, dibutyl tin dichloride, dibutyl tin dilaurate, dimethyl tin dichloride, or the like may be used.

The optical lens has more excellent optical characteristics.

Specifically, the optical lens has an excellent glass transition temperature (Tg). For example, the optical lens may have a glass transition temperature (Tg) of 75° C. or higher, 80° C. or higher, 85° C. or higher, or 88° C. or higher, specifically in the range of 75 to 120° C., in the range of 80 to 120° C., in the range of 95 to 120° C., in the range of 80 to 100° C., in the range of 85 to 100° C., or in the range of 85 to 90° C.

Further, the optical lens is colorless and transparent and is excellent in such optical characteristics as refractive index and Abbe number.

The optical lens may have a refractive index in the range of 1.50 to 1.75, in the range of 1.50 to 1.70, in the range of 1.50 to 1.65, or in the range of 1.55 to 1.65.

The optical lens may have an Abbe number of 20 or more, more specifically 30 or more. For example, the optical lens may have an Abbe number in the range of 20 to 50, in the range of 25 to 50, in the range of 30 to 45, in the range of 30 to 43, in the range of 35 to 43, in the range of 36 to 43, in the range of 37 to 43, in the range of 36 to 40, or in the range of 37 to 40.

The optical lens may have a light transmittance, for example, a light transmittance at a wavelength of 550 nm of 85.0% to 99.9%, more specifically 87.0% to 99.0% or 87.0% to 95.0%.

The optical lens may have a yellow index (YI) of 25 or less or 20 or less. Specifically, it may be in the range of 1 to 25, in the range of 1 to 20, in the range of 3 to 20, or in the range of 5 to 15.

According to an example, the optical lens may have a yellow index (YI) of 1 to 20 and a light transmittance at a wavelength of 550 nm of 85.0 to 99.9%. In addition, the optical lens may have an Abbe number of 30 to 45 and a glass transition temperature (Tg) of 75 to 120° C.

Further, an embodiment provides a process for producing an optical lens, which comprises (A) providing an isocyanate composition, (B) providing a thiol-based compound, (C) providing a polymerizable composition that comprises the isocyanate composition and the thiol-based compound, and (D) curing the polymerizable composition, wherein the isocyanate composition comprises a chlorine-based storage stabilizer and $H_6XDI$, the content of chlorine derived from the chlorine-based storage stabilizer in the isocyanate composition is 22 to 500 ppm, and the content of the NCO groups contained in the isocyanate composition is 42 to 45% by weight.

The isocyanate composition may be prepared by the steps of (1) Obtaining a composition that comprises $H_6XDI$ from cyclohexyldi(methylamine) by a process for synthesizing an isocyanate; and (2) adding a chlorine-based storage stabilizer to the composition that comprises $H_6XDI$ obtained in the above step (2) to adjust the content of chlorine contained in the composition that comprises $H_6XDI$ to 22 to 500 ppm.

In such event, the steps (1) and (2) in the process for producing an optical lens may be carried out according to the conditions and procedures as described above with regard to the steps (1) and (2) of the process for preparing an $H_6XDI$ composition. If necessary, the step of heat distillation for removing excess chlorine as exemplified above may be further carried out.

Thereafter, the composition that comprises $H_6XDI$ is mixed with a thiol-based compound, which is heated and cured in a mold to produce an optical lens. For this purpose, the composition that comprises $H_6XDI$ is mixed with a thiol-based compound to produce a polymerizable composition, which is degassed under reduced pressures and then injected into a mold for molding an optical lens. Such degassing and mold injection may be carried out in a temperature range of, for example, 20 to 40° C.

Once the composition is injected into the mold, polymerization is usually carried out by gradually heating the composition from a low temperature to a high temperature. In such event, the reaction temperature may be 30 to 150° C. or 40 to 130° C. In addition, a catalyst, which is conventionally used in the production of polythiourethane, may be employed in order to control the reaction rate. The specific types thereof are as exemplified above.

The polythiourethane article prepared according to the above process is released from the mold to obtain an optical lens.

The isocyanate composition according to the embodiments contains a certain amount of chlorine to improve the stability, so that the degradation of the reactivity can be prevented even when it is stored for a long period of time. Therefore, even if an isocyanate composition prepared according to the embodiments is used after storage thereof for a long period of time after the preparation thereof, the isocyanate composition can be polymerized with a thiol-based compound to produce a polythiourethane-based optical material having excellent properties in terms of refractive index, Abbe number, transparency, glass transition temperature, yellow index, and the like. It can be advantageously used for eyeglass lenses, camera lenses, and the like.

Best Mode for Carrying out the Invention

Hereinafter, the present invention is explained in detail by Examples. The following Examples are intended to further illustrate the present invention, and the scope of the Examples is not limited thereto.

EXAMPLE

Examples 1: Preparation of an Isocyanate Composition
(1) Preparation of Raw Materials 5 parts by weight of (3-(aminomethyl)cyclohexyl)methanamine was dissolved in 78 parts by weight of o-dichlorobenzene to prepare an amine solution. Thereafter, 44 parts by weight of phosgene was dissolved in 52 parts by weight of o-dichlorobenzene to prepare a solution, which was cooled to 10° C. with a brine condenser and then placed in a reaction vessel. The amine solution prepared above was slowly added thereto at a temperature of 50° C. or lower. In such event, the amount of the amine solution added was adjusted such that 5 moles of phosgene was added per 1 mole of amine. Thereafter, the reaction vessel was sealed, and the reaction solution was stirred for 2 hours. After further reaction for 3 hours at a temperature of 140° C. and a pressure of 3 kg/cm$^2$, the hydrochloric acid gas produced during the reaction was discharged. Upon completion of the reaction, the excessive phosgene was removed by a distillation process. The product was purified by fractional distillation under a reduced pressure to produce a composition comprising $H_6XDI$.

(2) Adjustment of Chlorine Content

A chlorine-based storage stabilizer was added to the composition comprising $H_6XDI$ obtained above as shown in the following Table 1 to prepare isocyanate compositions 1 to 7 having various chlorine contents.

Specifically, the step of adding a chlorine ion was carried out by injecting chlorine gas while the composition comprising $H_6XDI$ was stirred at room temperature for 1 hour to dissolve it, and then the undissolved chlorine gas was removed under a reduced pressure for about 30 minutes. In addition, the step of adding a chlorine-based storage stabilizer was carried out by adding each of the chlorine-based storage stabilizers listed in Table 1 below, followed by sufficient stirring at 35° C. for about 1 hour.

Thereafter, if excessive chlorine was present in the composition as measured by combustion ion chromatography, the composition was subjected to distillation at 80° C. to remove the chlorine ion and/or chlorine-based compound. Then, the chlorine content was measured again; and, if necessary, the above steps were repeated.

Example 2: Production of an Optical Lens

Isocyanate compositions were prepared in the same manner as in Example 1, except that the chlorine-based storage stabilizer was used as described in Evaluation Example 1 below.

Specifically, 520 g of the isocyanate composition, 479.3 g of 3,3'-thiobis[2-[(2-mercaptoethyl)thio]-1-propanethiol], 0.15 g of dibutyl tin dichloride as a curing catalyst, and 0.80 g of Zelec™ UN as an internal mold release agent were mixed uniformly to prepare a polymerizable composition. Then, the polymerizable composition was mixed at a reduced pressure in a nitrogen atmosphere for 30 minutes to remove bubbles and then filtered through a Teflon filter of 3 μm. The filtered polymerizable composition was injected into a glass mold assembled with an adhesive tape using nitrogen pressure. The glass mold injected with the polymerizable composition was placed in a forced circulation oven, and the temperature was elevated from 25° C. to 120° C. at a rate of 5° C./min, followed by polymerization at 120° C. for 18 hours. Thereafter, the polymerized resin was further cured at 130° C. for 4 hours, and a lens was released from the glass mold to obtain each optical lens having a center thickness of 1.2 mm.

Evaluation Example

Evaluation Examples 1: Evaluation of an Isocyanate Composition

The isocyanate composition prepared in Example 1 was evaluated for the storage stability in accordance with the method as described below. The results are shown in Table 1 to 3 below.

(1) Evaluation of Storage Stability of Isocyanate Compositions with Respect to the Chlorine Content The initial NCO content (NCO %) of the isocyanate compositions 1 to 7 whose chlorine content had been adjusted in Example 1 was measured by a back-titration method. First, an excess of n-butylamine relative to the theoretical NCO content was added and reacted, and the excessive n-butylamine that remained was analyzed with a 0.1 N hydrochloric acid reagent. The results are shown in Table 1 below.

In addition, Table 1 also summarizes the initial color of the isocyanate compositions, whether cloudiness occurred, and whether precipitates were present. The cloudiness and precipitates were determined by placing the isocyanate composition in a clear glass bottle, filling the bottle with nitrogen, and sealing it, which was then allowed to stand for one day or longer, and the appearance and the presence of precipitated materials on the bottom were observed. In such event, if the glass bottle containing the composition was transparent or no precipitate was generated, it was evaluated to be X. If it was cloudy or a precipitate was generated, it was evaluated to be °. In addition, if the amount of precipitates generated was 1% or less based on the total weight of the composition, it was evaluated to be X. If it exceeded 1%, it was evaluated to be °.

Thereafter, the isocyanate compositions 1 to 7 were stored at a temperature of 80° C. for 6 months. The NCO % of the isocyanate compositions 1 to 7 was measured in accordance with the method described above. The color, whether cloudiness occurred, and whether precipitates were present were evaluated. The method and criteria of evaluation are as described above. The results are shown in Table 1 below.

TABLE 1

| Isocyanate Composition | Chlorine-based storage stabilizer | Chlorine (ppm) | Initial | | | | After 6 months (@80° C.) | | | |
|---|---|---|---|---|---|---|---|---|---|---|
| | | | NCO % | Color | C* | P* | NCO % | Color | C* | P* |
| Composition 1 | Benzoyl chloride | 20 | 43.3 | Transparent | X | X | 40.3 | Transparent | ○ | ○ |
| Composition 2 | Chlorine ion | 50 | 43.3 | Transparent | X | X | 43.3 | Transparent | X | X |
| Composition 3 | Benzoyl chloride | 200 | 43.3 | Transparent | X | X | 43.3 | Transparent | X | X |
| Composition 4 | Chlorine ion + Benzoyl chloride | 370 | 43.3 | Transparent | X | X | 43.3 | Transparent | X | X |
| Composition 5 | Chlorine ion + Benzoyl chloride | 500 | 43.3 | Transparent | X | X | 43.3 | Transparent | X | X |
| Composition 6 | Chlorine ion + Benzoyl chloride | 610 | 43.3 | Transparent | X | X | 43.3 | Yellowing | X | X |
| Composition 7 | Benzoyl chloride | 800 | 43.3 | Transparent | X | X | 43.3 | Yellowing | X | X |

*C: cloudiness; P: precipitate

As confirmed from Table 1 above, the isocyanate compositions (compositions 2 to 5) having a chlorine content within 22 to 500 ppm retained a transparent color with almost no changes in the NCO % after storage for 6 months and without any cloudiness and precipitates. Thus, their stability was excellent even when they were stored for a long period of time.

In contrast, the other isocyanate compositions having a chlorine content of less than 22 ppm or more than 500 ppm changed to yellow or had cloudiness or precipitates after storage for 6 months, indicating decreased stability when they were stored for a long period of time.

(2) Evaluation of Storage Stability of Isocyanate Compositions with Respect to the Container The initial metal concentration of the isocyanate compositions 1 to 7 whose chlorine content had been adjusted in Example was measured. Then, they were each stored at 80° C. for 6 months in a container made of different materials, and the concentration of the residual metal ions was measured.

Table 2 shows analysis results of the samples stored in stainless steel (SUS 304) containers, and Table 2 shows those of the samples stored in steel containers whose interior had been coated with polyethylene.

TABLE 2

| Isocyanate Composition | Chlorine (ppm) | Stored in stainless steel containers | | | | | | | |
|---|---|---|---|---|---|---|---|---|---|
| | | Initial (ppm) | | | | After 6 months (@80° C.) | | | |
| | | Cr | Fe | Mn | Ni | Cr | Fe | Mn | Ni |
| Composition 1 | 20 | <0.1 | <0.1 | <0.1 | <0.1 | <0.1 | <0.1 | <0.1 | <0.1 |
| Composition 2 | 50 | <0.1 | <0.1 | <0.1 | <0.1 | <0.1 | 0.4 | <0.1 | <0.1 |
| Composition 3 | 200 | <0.1 | <0.1 | <0.1 | <0.1 | <0.1 | 0.8 | <0.1 | <0.1 |
| Composition 4 | 370 | <0.1 | <0.1 | <0.1 | <0.1 | <0.1 | 3.2 | <0.1 | 4.3 |
| Composition 5 | 500 | <0.1 | <0.1 | <0.1 | <0.1 | 0.5 | 13 | 5.5 | 6.0 |
| Composition 6 | 610 | <0.1 | <0.1 | <0.1 | <0.1 | 1.8 | 35 | 20 | 39 |
| Composition 7 | 800 | <0.1 | <0.1 | <0.1 | <0.1 | 3.6 | 99 | 85 | 67 |

TABLE 3

| Isocyanate Composition | Chlorine (ppm) | Stored in steel containers whose interior had been coated with polyethylene | | | | | | | |
|---|---|---|---|---|---|---|---|---|---|
| | | Initial (ppm) | | | | After 6 months (@80° C.) | | | |
| | | Cr | Fe | Mg | Ni | Cr | Fe | Mg | Ni |
| Composition 1 | 20 | <0.1 | <0.1 | <0.1 | <0.1 | <0.1 | <0.1 | <0.1 | <0.1 |
| Composition 2 | 50 | <0.1 | <0.1 | <0.1 | <0.1 | <0.1 | <0.1 | <0.1 | <0.1 |
| Composition 3 | 200 | <0.1 | <0.1 | <0.1 | <0.1 | <0.1 | <0.1 | <0.1 | <0.1 |
| Composition 4 | 370 | <0.1 | <0.1 | <0.1 | <0.1 | <0.1 | <0.1 | <0.1 | <0.1 |
| Composition 5 | 500 | <0.1 | <0.1 | <0.1 | <0.1 | <0.1 | <0.1 | <0.1 | <0.1 |
| Composition 6 | 610 | <0.1 | <0.1 | <0.1 | <0.1 | <0.1 | <0.1 | <0.1 | <0.1 |
| Composition 7 | 800 | <0.1 | <0.1 | <0.1 | <0.1 | <0.1 | <0.1 | <0.1 | <0.1 |

As shown in Tables 2 and 3, when the isocyanate composition was stored in a stainless steel container, the amount of metal eluted was greatly increased as the chlorine content in the composition was increased. In contrast, when it was stored in a steel container coated with polyethylene, a very small amount of metal was eluted even when the chlorine content in the composition was increased.

Evaluation Example 2: Evaluation of Optical Lenses

The optical lenses produced in Example 2 were evaluated for the physical properties according to the following methods. The results are shown in Table 4 below.

(1) Refractive Index and Abbe Number

The refractive index and Abbe number of the optical lens was measured at 20° C. using an Abbe refractometer DR-M4 (Atago Co.).

(2) Yellow Index and Light Transmittance

The optical lenses were each measured for chromaticity coordinates x and y using a spectrophotometer CT-210 manufactured by Minolta Co., from which their yellow indices were calculated with Equation 1 below. In addition, the transmittance at a wavelength of 550 nm was measured from the spectrum obtained using the same instrument.

$$Y.I = (234x + 106y + 106)/y \quad \text{[Equation 1]}$$

(3) Glass Transition Temperature (Tg, ° C.)

The glass transition temperature of the optical lens was measured with TMA Q400 (TA instruments Co.) under the penetration method (load of 50 g, pin line of 0.5 mm Φ, temperature elevation rate of 10° C./min)

(4) Stria 100 optical lenses were each observed with the naked eyes under a mercury lamp. The lenses with non-uniformity were determined to have stria, and the percentages were calculated. As a result, if the generation of stria was less than 5%, it was evaluated to be good. If it was 5% or more, it was evaluated to be poor.

TABLE 4

| Isocyanate Composition | Chlorine (ppm) | Refractive index (nd) | Abbe number (ve) | Light transmittance (%) | Tg (° C.) | Yellow index (Y.I.) | Stria |
|---|---|---|---|---|---|---|---|
| Composition 1 | 20 | Not measurable | Not measurable | 65 | 75 | 10 | Poor |
| Composition 2 | 50 | 1.6322 | 37 | 87 | 90 | 12 | Good |
| Composition 3 | 200 | 1.6331 | 38 | 87 | 91 | 12 | Good |
| Composition 4 | 370 | 1.6333 | 38 | 89 | 88 | 11 | Good |
| Composition 5 | 500 | 1.6312 | 39 | 88 | 90 | 10 | Good |
| Composition 6 | 610 | 1.6321 | 36 | 80 | 90 | 25 | Poor |
| Composition 7 | 800 | 1.6322 | 35 | 70 | 89 | 46 | Poor |

As confirmed from Table 4 above, when the isocyanate compositions (compositions 2 to 5) having a chlorine content of 22 to 500 ppm were used to produce lenses after storage for 6 months, the lenses produced therefrom were excellent in all of the refractive index, Abbe number, transmittance, Tg, and yellow index. In contrast, when the isocyanate compositions(compositions 1, 6, and 7) having a chlorine content of less than 22 ppm or greater than 500 ppm were used to produce lenses after storage for 6 months, the lenses produced therefrom were poor at least one of the refractive index, Abbe number, transmittance, Tg, yellow index, and stria.

This attributes to the fact that the chlorine content significantly affects the reactivity of $H_6XDI$. Specifically, if the chlorine content in the isocyanate composition is less than 22 ppm, the storage stability of the composition is deteriorated due to the excessive reactivity of $H_6XDI$, and the reaction becomes too rapid when it is used to produce a lens, resulting in nonuniform optical characteristics thereof. If the chlorine content exceeds 500 ppm, it is expected that the reactivity suppression effect of $H_6XDI$ is excessive, so that the reaction and/or curing in the production of a lens would not take place, which lowers the optical characteristics thereof.

The invention claimed is:

1. An isocyanate composition, which comprises a chlorine-based storage stabilizer and hydrogenated xylylene diisocyanate ($H_6XDI$),
    wherein the amount of $H_6XDI$ in the isocyanate composition is 90% by weight or more,
    wherein the content of chlorine in the entire composition is 22 to 500 ppm,
    wherein the chlorine-based storage stabilizer comprises at least one selected from the group consisting of a chlorine ion, benzotrichloride, benzyl chloride, benzoyl chloride, and a $C_{1-10}$ alkanoyl chloride, and
    wherein the content of the NCO groups contained in the entire composition is 42 to 45% by weight,
    wherein when the isocyanate composition is left at a temperature of 80° C. for 6 months, the amount of precipitates generated is 1% by weight or less based on the total weight of the composition, and
    wherein the difference in the content of the NCO groups between the initial composition and the composition left at a temperature of 80° C. for 6 months is 5% by weight or less.

2. The isocyanate composition of claim 1, wherein the chlorine-based storage stabilizer comprises a chlorine ion.

3. The isocyanate composition of claim 1, wherein the chlorine-based storage stabilizer is selected from the group consisting of benzotrichloride, benzyl chloride, benzoyl chloride, and a $C_{1-10}$ alkanoyl chloride.

4. The isocyanate composition of claim 1, wherein when the isocyanate composition is sealed and left in a container, the region of which in contact with the composition is not reactive with chlorine, at a temperature of 80° C. for 6 months, the difference in the content of the NCO groups between the initial composition and the composition after 6 months is 4% by weight or less.

5. An isocyanate composition, which comprises a chlorine-based storage stabilizer and hydrogenated xylylene diisocyanate ($H_6XDI$),
    wherein the amount of $H_6XDI$ in the isocyanate composition is 90% by weight or more,
    wherein the content of the NCO groups contained in the entire composition is 42 to 45% by weight;
    wherein the chlorine-based storage stabilizer comprises at least one selected from the group consisting of a chlorine ion, benzotrichloride, benzyl chloride, benzoyl chloride, and a $C_{1-10}$ alkanoyl chloride, and
    wherein when the isocyanate composition is left at a temperature of 80° C. for 6 months, the amount of precipitates generated is 1% by weight or less based on the total weight of the composition, and
    wherein the difference in the content of the NCO groups between the initial composition and the composition left at a temperature of 80° C. for 6 months is 5% by weight or less.

6. A process for preparing an isocyanate composition, which comprises (1) producing a composition that comprises hydrogenated xylylene diisocyanate ($H_6XDI$) from cyclohexyldi(methylamine) by a process for synthesizing an isocyanate; and
    (2) adjusting the content of chlorine contained in the composition that comprises hydrogenated xylylene diisocyanate to 22 to 500 ppm,
    wherein when the isocyanate composition is sealed and left at a temperature of 80° C. for 6 months, the amount of precipitates generated is 1% by weight or less based on a total weight of the composition, and a difference in the content of the NCO groups between the initial composition and the composition left at a temperature of 80° C. for 6 months is 5% by weight or less,
    wherein the amount of $H_6XDI$ in the isocyanate composition is 90% by weight or more,
    wherein the isocyanate composition comprises a chlorine-based storage stabilizer,
    wherein the chlorine-based storage stabilizer comprises at least one selected from the group consisting of a chlorine ion, benzotrichloride, benzyl chloride, benzoyl chloride, and a $C_{1-10}$ alkanoyl chloride.

7. The process for preparing an isocyanate composition of claim 6, wherein the step (2) is carried out by adding to the composition that comprises $H_6XDI$ at least one chlorine-based storage stabilizer selected from the group consisting of benzotrichloride, benzyl chloride, benzoyl chloride, and a $C_{1-10}$ alkanoyl chloride, or containing a chlorine ion.

8. The process for preparing an isocyanate composition of claim 6, wherein the step (2) further comprises subjecting the composition that comprises $H_6XDI$ to heat distillation.

9. A polymerizable composition, which comprises an isocyanate composition and a thiol-based compound,
    wherein the isocyanate composition comprises a chlorine-based storage stabilizer and hydrogenated xylylene diisocyanate ($H_6XDI$),
    wherein the amount of $H_6XDI$ in the isocyanate composition is 90% by weight or more,
    wherein the content of chlorine in the isocyanate composition is 22 to 500 ppm,
    wherein the chlorine-based storage stabilizer comprises at least one selected from the group consisting of a chlorine ion, benzotrichloride, benzyl chloride, benzoyl chloride, and a $C_{1-10}$ alkanoyl chloride, and
    wherein the content of the NCO groups contained in the isocyanate composition is 42 to 45% by weight,
    wherein when the isocyanate composition is left at a temperature of 80° C. for 6 months, the amount of precipitates generated is 1% by weight or less based on the total weight of the composition, and
    wherein the difference in the content of the NCO groups between the initial composition and the composition left at a temperature of 80° C. for 6 months is 5% by weight or less.

10. An optical lens, which comprises a polythiourethane formed by curing a polymerizable composition that comprises an isocyanate composition and a thiol-based compound,
  wherein the isocyanate composition comprises a chlorine-based storage stabilizer and hydrogenated xylylene diisocyanate ($H_6XDI$),
  wherein the amount of $H_6XDI$ in the isocyanate composition is 90% by weight or more,
  wherein the content of chlorine in the isocyanate composition is 22 to 500 ppm,
  wherein the chlorine-based storage stabilizer comprises at least one selected from the group consisting of a chlorine ion, benzotrichloride, benzyl chloride, benzoyl chloride, and a $C_{1-10}$ alkanoyl chloride,
  wherein the content of the NCO groups contained in the isocyanate composition is 42 to 45% by weight,
  wherein when the isocyanate composition is left at a temperature of 80° C. for 6 months, the amount of precipitates generated is 1% by weight or less based on the total weight of the composition, and
  wherein the difference in the content of the NCO groups between the initial composition and the composition left at a temperature of 80° C. for 6 months is 5% by weight or less.

11. The optical lens of claim 10, which has a yellow index (YI) of 1 to 20 and a light transmittance of 85.0 to 99.9% at a wavelength of 550 nm.

12. The optical lens of claim 10, which has an Abbe number of 30 to 45 and a glass transition temperature of 75 to 120° C.

13. A process for producing an optical lens, which comprises:
  (A) providing an isocyanate composition,
  (B) providing a thiol-based compound,
  (C) providing a polymerizable composition that comprises the isocyanate composition and the thiol-based compound, and
  (D) curing the polymerizable composition,
  wherein the isocyanate composition comprises a chlorine-based storage stabilizer and hydrogenated xylylene diisocyanate ($H_6XDI$),
  wherein the amount of $H_6XDI$ in the isocyanate composition is 90% by weight or more,
  wherein the content of chlorine in the isocyanate composition is 22 to 500 ppm,
  wherein the chlorine-based storage stabilizer comprises at least one selected from the group consisting of a chlorine ion, benzotrichloride, benzyl chloride, benzoyl chloride, and a $C_{1-10}$ alkanoyl chloride, and
  wherein the content of the NCO groups contained in the isocyanate composition is 42 to 45% by weight,
  wherein when the isocyanate composition is left at a temperature of 80° C. for 6 months, the amount of precipitates generated is 1% by weight or less based on the total weight of the composition, and
  wherein the difference in the content of the NCO groups between the initial composition and the composition left at a temperature of 80° C. for 6 months is 5% by weight or less.

* * * * *